US009737408B2

(12) United States Patent
Leszko et al.

(10) Patent No.: US 9,737,408 B2
(45) Date of Patent: Aug. 22, 2017

(54) TIBIAL IMPACTION GUIDE SURGICAL INSTRUMENT AND METHOD OF USING SAME

(71) Applicant: DEPUY IRELAND UNLIMITED COMPANY, CO Cork OT (IE)

(72) Inventors: Filip Leszko, Winona Lake, IN (US); Jonathan C. Lee, Mishawaka, IN (US); Craig S. Tsukayama, Fort Wayne, IN (US)

(73) Assignee: DEPUY IRELAND UNLIMITED COMPANY (IE)

( * ) Notice: Subject to any disclaimer, the term of this patent is extended or adjusted under 35 U.S.C. 154(b) by 1103 days.

(21) Appl. No.: 13/833,208

(22) Filed: Mar. 15, 2013

(65) Prior Publication Data

US 2014/0277540 A1 Sep. 18, 2014

(51) Int. Cl.
*A61B 17/16* (2006.01)
*A61F 2/38* (2006.01)
*A61F 2/46* (2006.01)
*A61F 2/30* (2006.01)

(52) U.S. Cl.
CPC ............ *A61F 2/389* (2013.01); *A61F 2/3859* (2013.01); *A61F 2/461* (2013.01); *A61F 2002/3069* (2013.01); *A61F 2002/3082* (2013.01); *A61F 2002/30332* (2013.01); *A61F 2002/30594* (2013.01); *A61F 2002/30616* (2013.01); *A61F 2002/30736* (2013.01); *A61F 2002/30878* (2013.01); *A61F 2002/30884* (2013.01); *A61F 2002/4687* (2013.01)

(58) Field of Classification Search
CPC ...................... A61F 2/389; A61F 2/461; A61F 2002/30594; A61F 2002/30884; A61F 2002/30897; A61B 17/1764; A61B 17/921
See application file for complete search history.

(56) References Cited

U.S. PATENT DOCUMENTS

| D372,309 S | 7/1996 | Heldreth | |
|---|---|---|---|
| 2008/0119941 A1* | 5/2008 | Seo | A61F 2/461 623/20.34 |
| 2009/0036909 A1* | 2/2009 | Perry | A61F 2/461 606/157 |
| 2012/0123429 A1* | 5/2012 | Beedall | A61F 2/461 606/99 |
| 2013/0006252 A1* | 1/2013 | Waite, II | A61B 17/1764 606/88 |
| 2014/0094812 A1* | 4/2014 | Edwards | A61F 2/461 606/88 |
| 2014/0094821 A1* | 4/2014 | Wagner | A61F 2/461 606/99 |

* cited by examiner

*Primary Examiner* — Matthew Lawson
(74) *Attorney, Agent, or Firm* — Barnes & Thornburg LLP

(57) ABSTRACT

An orthopaedic surgical instrument includes a cup including an outer surface having an opening positioned on a component-engaging side and an inner wall extending from the opening of the outer surface to a back wall. The inner wall having a plurality of stepped surfaces facing the component-engaging side. Each of the plurality of stepped surfaces is sized to receive a platform of a tibial tray.

20 Claims, 6 Drawing Sheets

TIBIAL IMPACTION GUIDE SURGICAL
INSTRUMENT AND METHOD OF USING
SAME

TECHNICAL FIELD

The present disclosure relates generally to orthopaedic instruments for use in the performance of an orthopaedic joint replacement procedure, and more particularly to orthopaedic surgical instruments for use in the performance of a revision knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a platform having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared intramedullary canal of the patient's tibia, and the femoral component is configured to be coupled to a surgically-prepared distal end of a patient's femur.

From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During a revision knee surgery, the orthopaedic surgeon typically uses a variety of different orthopaedic surgical instruments such as, for example, cutting blocks, surgical reamers, drill guides, prosthetic trials, and other surgical instruments to prepare the patient's bones to receive the knee prosthesis.

SUMMARY

According to one aspect of the disclosure, an orthopaedic surgical instrument having a component-engaging side and a back side includes a cup positioned on the component-engaging side, the cup including an outer surface having an opening positioned on the component-engaging side, a slot defined in the cup, and a collar coupled to the outer surface of the cup toward the back side. The cup includes an inner wall extending from the opening of the outer surface to a back wall, the inner wall having a plurality of stepped surfaces facing the component-engaging side. The slot extends from the component-engaging side to the back side, through the outer surface and the inner wall. The collar includes an opening toward the back side sized to receive an impaction handle and a flange positioned in the opening that is configured to be secured to the impaction handle. Each of the plurality of stepped surfaces is sized to receive a platform of a tibial tray.

In some embodiments, each of the plurality of stepped surfaces may have a perimeter, and the perimeters of the plurality of stepped surfaces may decrease as the inner wall extends from the opening to the back wall. Additionally, in some embodiments, the back wall may be sized to receive a platform of a tibial tray. Additionally or alternatively, in some embodiments, each of the plurality of stepped surfaces may have a kidney-shaped perimeter configured to receive the platform of the tibial tray.

In some embodiments, the slot may be configured to align with a keel of the tibial tray to be received by the stepped surfaces. In some embodiments, the slot may be positioned on a medial side of the instrument. Alternatively, in some embodiments, the slot may be positioned on a lateral side of the instrument. Additionally or alternatively, in some embodiments, the instrument may further include a second slot defined in the cup that extends from the component-engaging side to the back side, through the outer surface and the inner wall of the cup. The second slot may be positioned on a medial side of the instrument.

In some embodiments, the instrument may further include a boss positioned on an anterior side of the outer surface of the cup, and an elongated alignment bore defined in the boss extending from the component-engaging side to the back side. The alignment bore may be sized to receive a shaft of an alignment rod.

In some embodiments, the instrument may further include a central aperture defined through the back wall of the cup and through the opening of the collar. The central aperture may be sized to receive a guide pin of the impaction handle and the flange is positioned adjacent to the central aperture. Additionally, in some embodiments, the collar may further include a recessed wall positioned adjacent to the flange to allow a catch of the impaction handle to engage the flange.

According to another aspect, a method of implanting a prosthetic component into a proximal end of a tibia is disclosed. The method includes securing an impaction guide to an end of an elongated impaction handle, fitting a platform of a tibial tray into one of a plurality of stepped surfaces of the impaction guide, inserting a stem coupled to the tibial tray into a surgically prepared intramedullary canal of the tibia, the intramedullary canal having a keel-punched slot, rotating the impaction handle axially to sight the slot of the intramedullary canal through a slot defined in the impaction guide, and advancing the tibial tray into the intramedullary canal using the impaction handle. In some embodiments, rotating the impaction handle axially may include rotating the impaction handle axially after partially inserting the stem into the intramedullary canal.

In some embodiments, securing the impaction guide may include engaging a flange of the impaction guide with a catch of the impaction handle, and clamping the impaction guide to the impaction handle.

According to another aspect, a method of implanting a prosthetic component into a proximal end of a tibia is disclosed. The method includes securing an impaction guide to an end of an elongated impaction handle, securing an alignment rod to the impaction guide, fitting a platform of a tibial tray into one of a plurality of stepped surfaces of the impaction guide, making a reference marking on the tibia, inserting a stem coupled to the tibial tray into a surgically prepared intramedullary canal of the tibia, the intramedullary canal having a keel-punched slot, rotating the impaction handle axially to position the alignment rod in a common imaginary plane with the reference mark on the tibia and a center of the intramedullary canal, and advancing the tibial tray into the intramedullary canal using the impaction handle. In some embodiments, securing the alignment rod may include sliding a shaft of the alignment rod through an elongated alignment bore defined in the impaction guide.

In some embodiments, making the reference marking may include marking the tibia using a surgical marking pen. Additionally or alternatively, in some embodiments, making the reference marking may include marking the tibia using an electrosurgical generator tool.

In some embodiments, rotating the impaction handle axially may include rotating the impaction handle axially after partially inserting the stem into the intramedullary canal.

In some embodiments, securing the impaction guide may include engaging a flange of the impaction guide with a catch of the impaction handle, and clamping the impaction guide to the impaction handle.

According to another aspect, the orthopaedic surgical instrument includes a cup including an outer surface having an opening positioned on a component-engaging side and an inner wall extending from the opening of the outer surface to a back wall. The inner wall having a plurality of stepped surfaces facing the component-engaging side. Each of the plurality of stepped surfaces is sized to receive a platform of a tibial tray.

BRIEF DESCRIPTION OF THE DRAWINGS

The detailed description particularly refers to the following figures, in which.

DETAILED DESCRIPTION OF THE DRAWINGS

Figure 1:
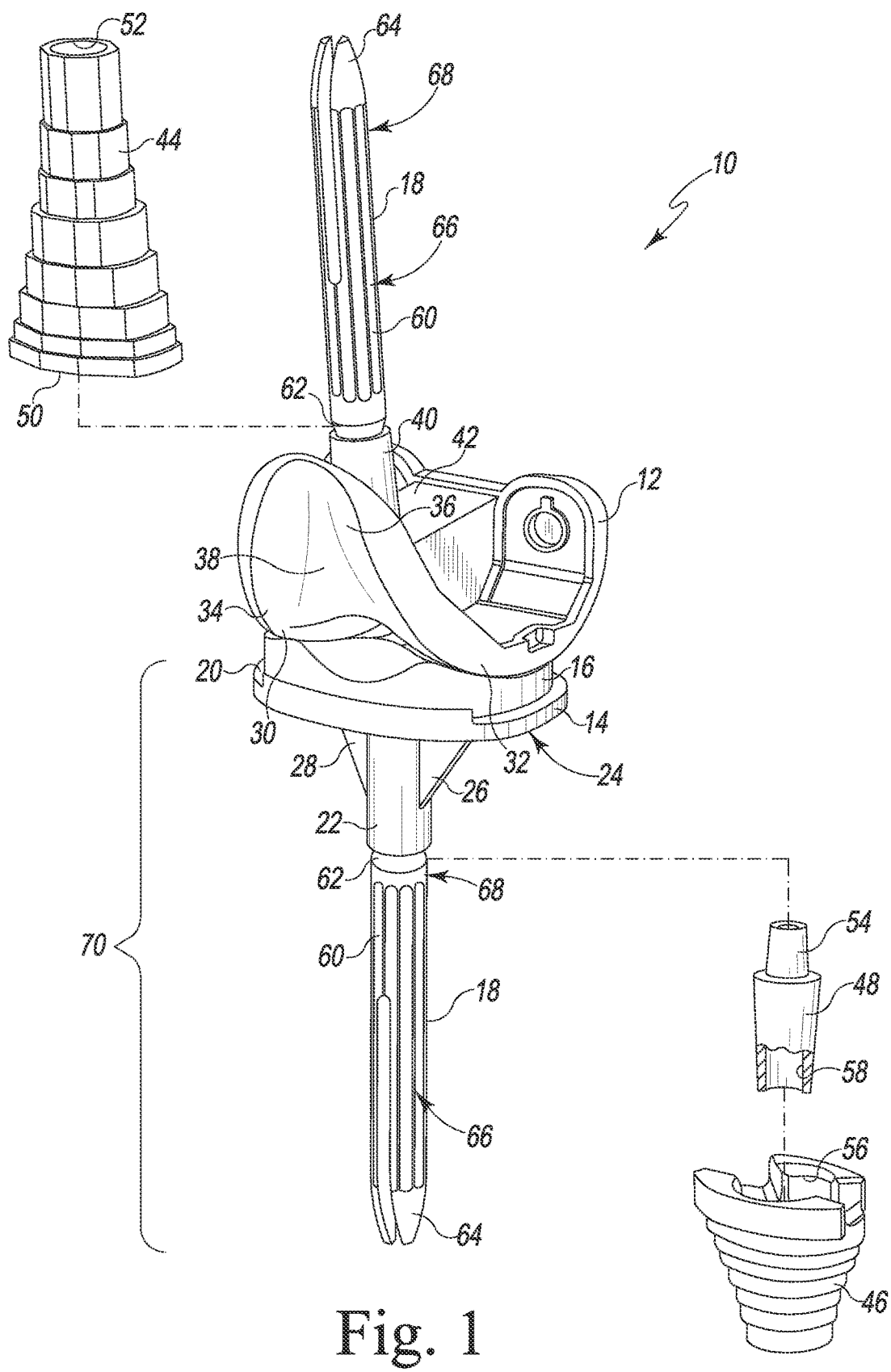
FIG. 1 is a perspective view of an orthopaedic knee prosthesis, note a pair of optional sleeve components and a sleeve adaptor are shown exploded from the assembled knee prosthesis, with a portion of the stem adaptor being cut away for clarity of description.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, there is shown an implantable knee prosthesis 10 for use in the performance of an orthopaedic knee replacement procedure. The knee prosthesis 10 includes a femoral component 12, a tibial tray 14, a bearing 16, and a number of stem components 18. Each of the variously-sized stem components 18 may be secured to either the tibial tray 14 or the femoral component 12.

The tibial tray 14 is configured to be implanted into a surgically-prepared end of a patient's proximal tibia (not shown). The tibial tray 14 includes a platform 20 having an elongated stem post 22 extending inferiorly away from its inferior surface 24. The tibial tray 14 includes a pair of keels 26, 28 connecting the stem post 22 and the inferior surface 24. The elongated tibial stem post 22 is configured to receive the stem components 18. Specifically, the stem post 22 of the tibial tray 14 has a tapered bore formed therein into which a tapered end of one of the stem components 18 may be advanced to taper lock the stem component 18 and the tibial tray 14 to one another. In such a way, the stem component 18 may then be implanted into a surgically-prepared (e.g., reamed, punched, or broached) intramedullary canal. When implanted, each of the keels 26, 28 engages a slot defined in the intramedullary canal to secure the tibial tray 14 to the bone.

The bearing 16 is securable to the tibial tray 14. In particular, the bearing 16 may be snap-fit to the tibial tray 14. In such a way, the bearing 16 is fixed relative to the tibial tray 14 (i.e., it is not rotatable or moveable in the anterior/posterior or medial/lateral directions). Although, in other embodiments, the bearing 16 may be secured in a manner that allows it to rotate relative to the tibial tray 14.

The bearing 16 includes a lateral bearing surface 30 and a medial bearing surface 32. The bearing surfaces 30, 32 are configured to articulate with a lateral condyle surface 34 and a medial condyle surface 36, respectively, of the femoral component 12. Specifically, the femoral component 12 is configured to be implanted into a surgically-prepared distal end of the patient's femur (not shown), and is configured to emulate the configuration of the patient's natural femoral condyles. As such, the lateral condyle surface 34 and the medial condyle surface 36 are configured (e.g., curved) in a manner which mimics the condyles of the natural femur. The lateral condyle surface 34 and the medial condyle surface 36 are spaced apart from one another thereby defining an intercondylar notch therebetween.

The condyle surfaces 34, 36 are formed in a bearing surface 38 of the femoral component 12. The femoral component 12 also includes an elongated stem post 40, extending superiorly away from its opposite backside surface 42. The elongated femoral stem post 40 is configured to receive the stem components 18. Specifically the femoral component 12 has a tapered bore formed therein into which a tapered end of one of the stem components 18 may be advanced to taper lock the stem component 18 and the femoral component 12 to one another. In such a way, the stem component 18 may then be implanted into a surgically-prepared (e.g., reamed or broached) intramedullary canal of the patient's femur.

The knee prosthesis 10 may also include a number of optional components such as a femoral sleeve component 44, a tibial sleeve component 46, and a stem adaptor 48. The sleeve components 44, 46 may be used to facilitate implantation of the femoral component 12 and the tibial tray 14, respectively, in the presence of reduced bone quality in the patient's femur or tibia. The femoral sleeve component 44 is configured to be secured to the femoral component 12 so as to be positioned between the femoral component 12 and the stem component 18. In particular, the inferior end 50 of the femoral sleeve component 44 has a bore (not shown) formed therein that may be taper locked to the outer surface of the femoral component's stem post 40 to lock the sleeve component 44 to the femoral component 12. The opposite, superior end of the femoral sleeve component 44 is configured to receive the stem components 18. Specifically, the superior end of the femoral sleeve component 44 has a tapered bore 52 formed therein into which a tapered end of one of the stem components 18 may be advanced to taper lock the stem component 18 and the femoral sleeve component 44 to one another.

The tibial sleeve component 46 may be embodied in a similar manner in which a bore formed in its superior end is taper locked to the stem post 22 of the tibial tray 14, with its opposite, inferior end being configured to receive the stem components 18 and thereby lock the stem component 18 and the tibial sleeve component 46 to one another.

Alternatively, the tibial sleeve component 46 may be used in conjunction with the stem adaptor 48. In such an embodiment, the stem adaptor 48 is used to secure both the stem components 18 and the tibial sleeve component 46 to the tibial tray 14. In particular, the stem adaptor 48 includes a tapered post 54 that is identical in shape and size to a tapered end of each of the stem components 18. As such, the tapered post 54 of the stem adaptor 48 may be advanced into the tibial tray's stem post 22 to lock the post 54 (and hence the stem adaptor 48) and the tibial tray 14 to one another. The tibial sleeve component 46 is configured to be secured to the stem adaptor 48 so as to be positioned between the tibial tray 14 and the stem component 18. In particular, the tibial sleeve component 46 has a bore 56 formed therein that extends through its entire length and hence is open to both its superior end and its inferior end. The tibial sleeve component 46 may be advanced over the stem adaptor 48 such that the tapered sidewalls forming the bore 56 of the tibial sleeve component 46 engage to the tapered outer surface of the stem adaptor 48 to taper lock the sleeve component 46 to the stem adaptor 48 to one another. The inferior end of the stem adaptor 48 has a tapered bore 58 formed therein into which a tapered end of one of the stem components 18 may be advanced to taper lock the stem component 18 and the stem adaptor 48 to one another.

The components of the knee prosthesis 10 that engage the natural bone, such as the femoral component 12, the tibial tray 14, the stem components 18, and the sleeve components 44, 46, along with the stem adaptor 48, may be constructed with an implant-grade biocompatible metal, although other materials may also be used. Examples of such metals include cobalt, including cobalt alloys such as a cobalt chrome alloy, titanium, including titanium alloys such as a Ti6Al4V alloy, and stainless steel. Such a metallic component may also be coated with a surface treatment, such as hydroxyapatite, to enhance biocompatibility. Moreover, the surfaces of the metallic components that engage the natural bone may be textured to facilitate securing the components to the bone. Such surfaces may also be porous coated to promote bone ingrowth for permanent fixation.

The bearing 16 may be constructed with a material that allows for smooth articulation between the bearing 16 and the femoral component 12, such as a polymeric material. One such polymeric material is polyethylene such as ultra-high molecular weight polyethylene (UHMWPE).

Each of the stem components 18 includes an elongated, generally cylindrical stem body 60. The elongated stem body 60 extends distally away from a tapered end 62 and terminates at rounded distal end 64 that defines the inferior-most surface of the stem component 18 when it is secured to a tibial tray 14 or the superior-most surface of the stem component 18 when it is secured to a femoral component 12.

A number of elongated flutes 66 are formed in the outer annularly-shaped surface 68 of the stem body 60. The longitudinal axis of each of the flutes 66 is parallel to the longitudinal axis of the stem component 18 and hence is arranged in the superior/inferior direction.

The stem component 18 may be provided in a number of different configurations in order to fit the needs of a given patient's anatomy. In particular, the stem component 18 may be configured in various different lengths to conform to the patient's anatomy (e.g., a relatively long stem component 18 for use with a long femur or tibia, a relatively short stem for use with a short femur or tibia, etcetera). In one illustrative embodiment, the stem component 18 may be provided in three different lengths (e.g., 60 mm, 110 mm, and 160 mm).

The stem component 18 may also be provided in varying body diameters to fit the needs of a given patient's anatomy. The body diameter of a given stem component 18 is the stem component's medial/lateral cross sectional width in the cylindrical midsection of the stem component's body 60 (i.e., not at its tapered end 62 or its distal tip 64). In one illustrative embodiment, the stem component 18 may be provided in eight different diameters (e.g., 10 mm, 12 mm, 14 mm, 16 mm, 18 mm, 20 mm, 22 mm, and 24 mm) at each of the three different lengths (e.g., 60 mm, 110 mm, and 160 mm). In other words, in such an illustrative embodiment, 24 differently-sized stem components 18 may be provided in eight different diameters and three different lengths.

Likewise, the femoral component 12, the tibial tray 14, and the sleeve components 44, 46 may be provided in various different sizes to fit the needs of a given patient's anatomy. However, each of the differently-sized stem components 18 is compatible with each of the differently-sized femoral components 12, tibial trays 14, and sleeve components 44, 46, along with the stem adaptor 48. In particular, the geometry of the tapered bores of each of the differently-sized tibial trays 14, the differently-sized femoral components 12, the differently-sized sleeve components 44, 46, and the stem adaptor 48 is identical. Likewise, the geometry of the tapered ends 62 of each of the differently-sized stem components 18 is identical.

When assembled for implantation, a tibial construct 70 is formed from the tibial tray 14, a stem component 18, and, optionally, the sleeve component 46 and/or the stem adaptor 48. As described below, a surgeon may insert the tibial construct 70 into the patient's tibia in a surgical procedure. During installation, the tibial construct 70 should be correctly aligned with the tibia to ensure secure fixation.

Referring now to FIGS. 2-5, an impaction guide 100 is shown. The impaction guide 100 includes a component-engaging side 102 that receives the platform 20 of the tibial tray 14 and a back side 104 opposite the component-engaging side 102. The impaction guide 100 further includes a cup 106 positioned on the component-engaging side 102 and a collar 108 coupled to the cup 106 and positioned on the back side 104.

Figure 2:
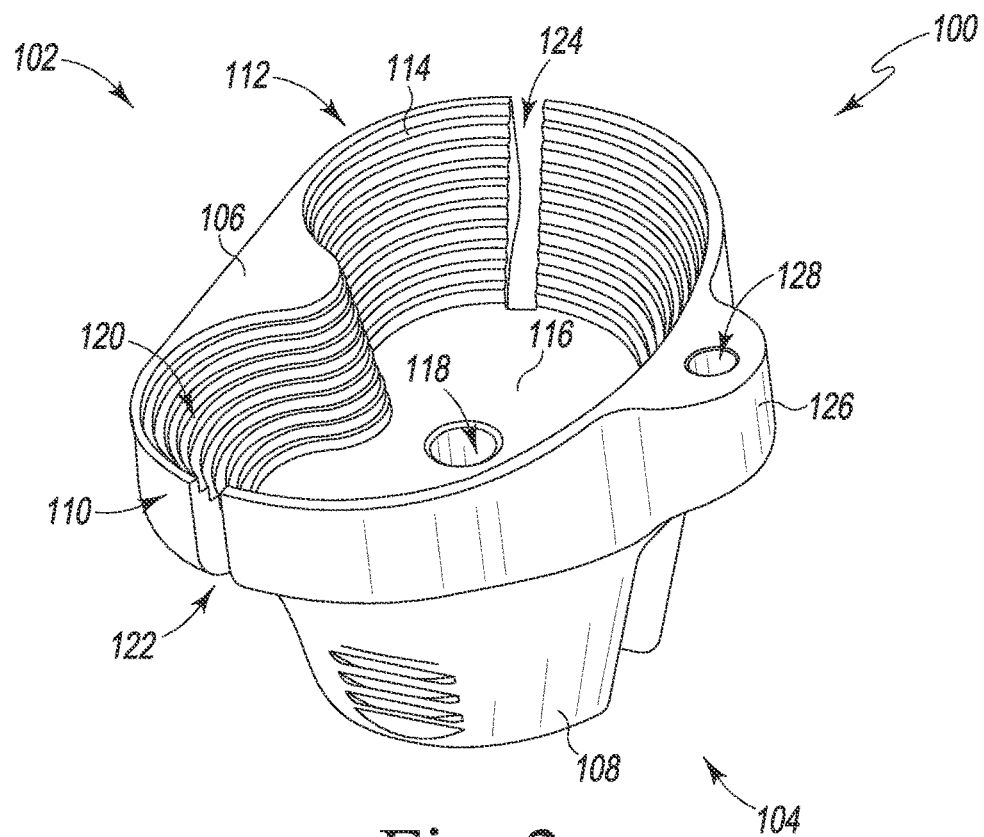
FIG. 2 is a perspective view of an orthopaedic surgical instrument tibial impaction guide.
Figure 4:
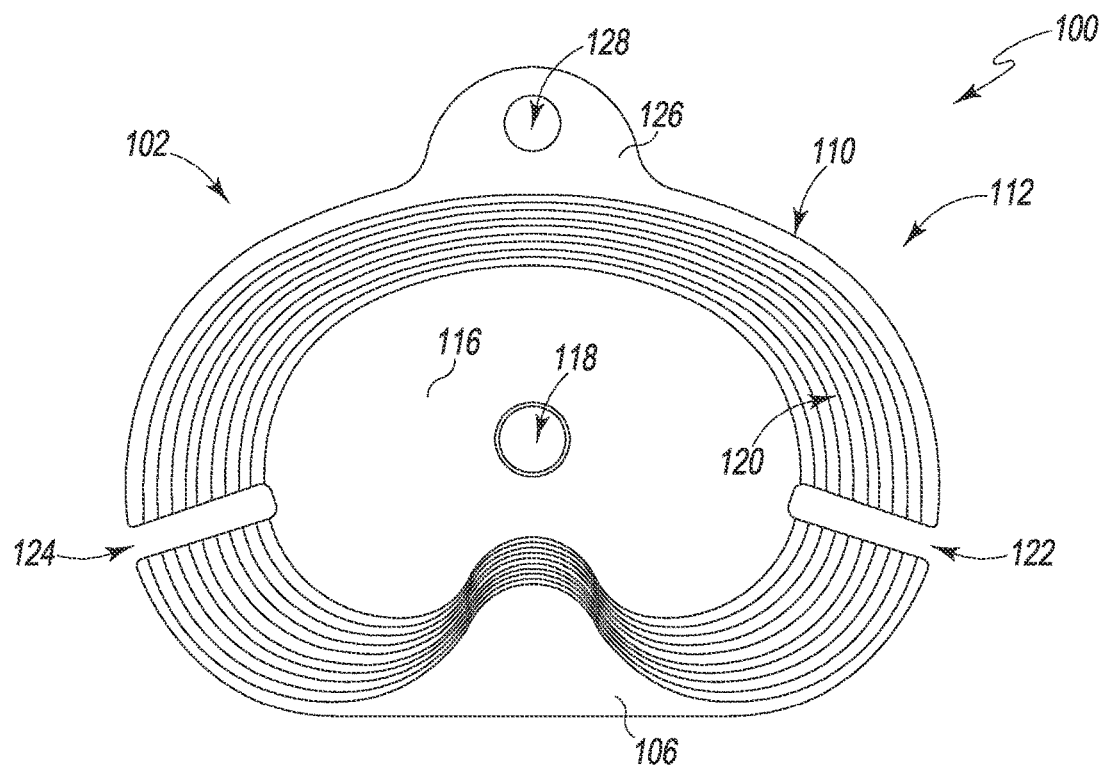
FIG. 4 is a plan view of the surgical instrument of FIGS. 2-3.
Figure 5:
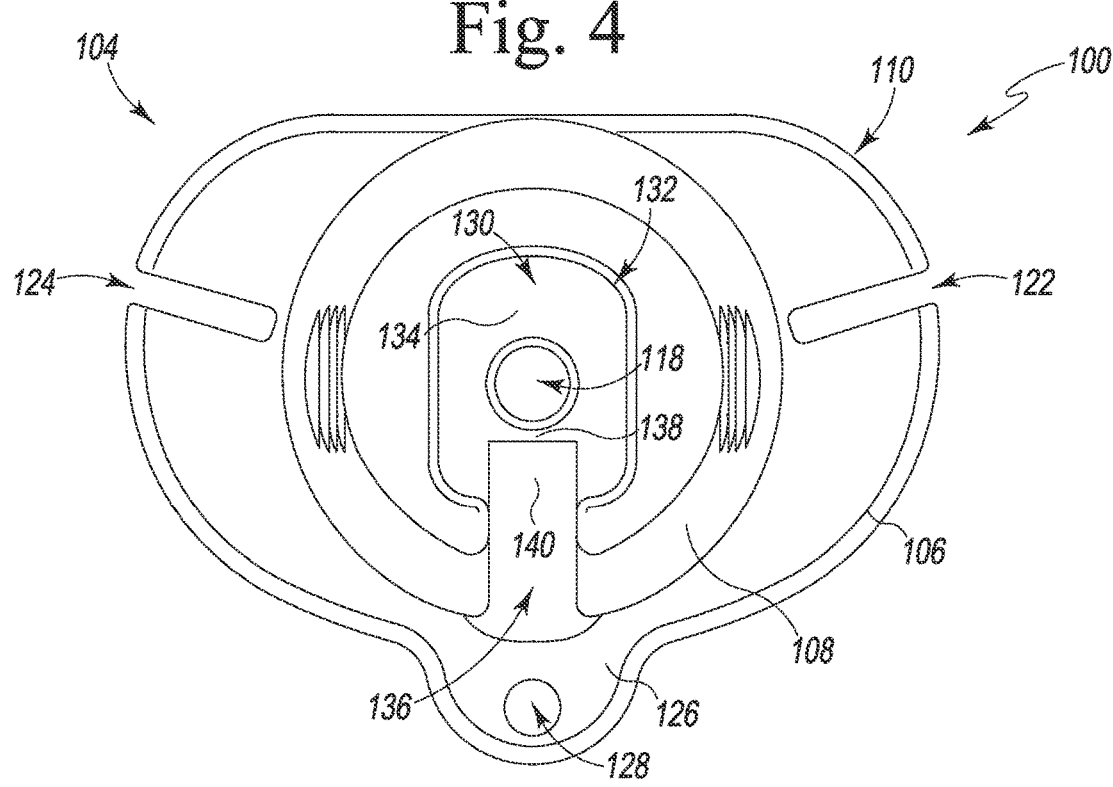
FIG. 5 is a back-side plan view of the surgical instrument of FIGS. 2-4.

The cup 106 includes an outer surface 110 extending from the component-engaging side 102 to the collar 108. As shown in FIGS. 2 and 4, the cup 106 has an opening 112 defined therein that is positioned on the component-engaging side 102. The cup 106 includes an inner wall 114 extending from the opening 112 to a substantially planar back wall 116. The inner wall 114 is terraced and includes a number of stepped surfaces 120.

The opening 112 of the cup 106 has a kidney-shaped perimeter that follows the shape of the platform 20 of a tibial tray 14. Similarly, the perimeter of each stepped surface 120 defines a kidney-shape that is configured to receive the platform 20 of one size of tibial tray 14. In the illustrative embodiment, each of the stepped surfaces 120 has negative geometry that matches the perimeter of the platform 20 of one tibial tray. As a result, the platform 20 of that tibial tray 14 may be fitted onto that stepped surface 120.

The perimeter of each of the stepped surfaces 120 decreases along the inner wall 114 toward the back wall 116. In other words, the inner wall 114 slopes inwardly toward the back wall 116. Thus, each of the plurality of stepped surfaces 120 may be configured to receive one size of a group of differently-sized tibial trays 14. For example, the illustrative impaction guide 100 includes ten stepped surfaces 120; as such, the guide 100 is configured to receive ten differently-sized tibial trays 14. In some embodiments, the back wall 116 may also be configured to receive a tibial tray 14. For example, another embodiment of the impaction guide 100 may include nine stepped surfaces 120 and the back wall 116 collectively configured to receive the ten differently-sized tibial trays 14.

The cup 106 of the guide 100 includes an indicator configured to indicate location of the keels 26, 28 of the tibial tray 14 when the tray is fitted into the cup 106. In the illustrative embodiment, the indicator includes a pair of slots 122, 124 that extend through the outer surface 110 and the inner wall 114 and are positioned on the medial and lateral sides of the impaction guide 100, respectively. The slots 122, 124 extend through each of the stepped surfaces 120, as shown in FIG. 2. Although the illustrative impaction guide 100 includes two slots 122, 124, other embodiments of the impaction guide 100 the indicator may include a single slot on the medial side or the lateral side. In other embodiments, the indicator may include a marking or etching in the outer surface 110 of the cup 106 that indicates the location of the keels 26, 28 of the tibial tray 14 when the tray is fitted into the cup 106.

Figure 3:
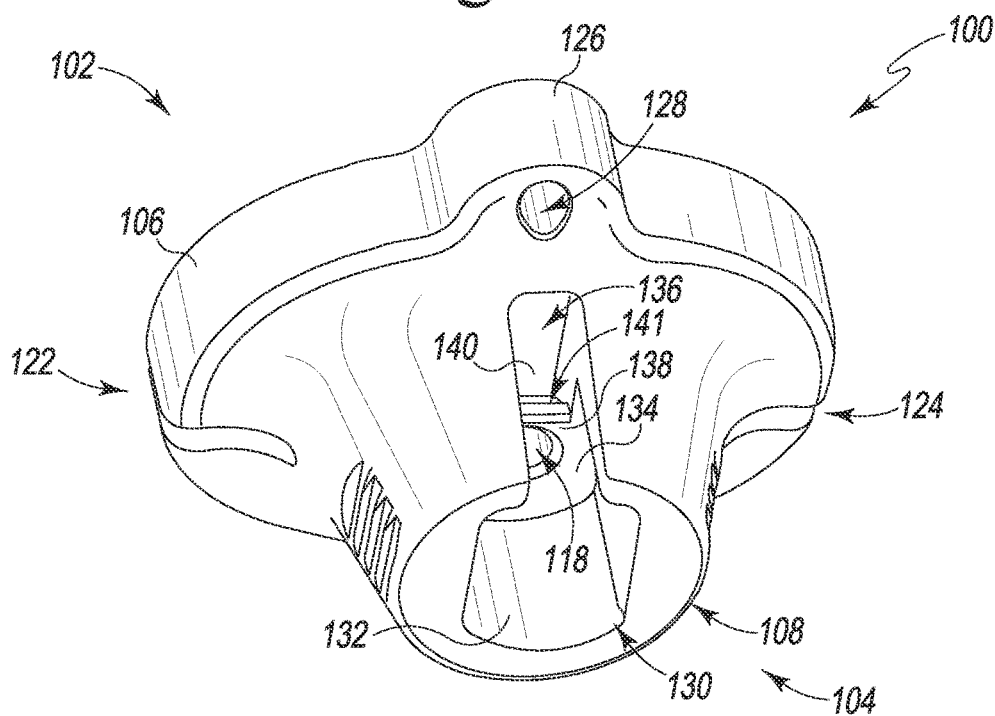
FIG. 3 is a back-side perspective view of the surgical instrument of FIG. 2.

The impaction guide 100 includes a boss 126 that extends the outer surface 110 of the cup 106 on the anterior side. As shown in FIGS. 2-3, the boss 126 has an elongated alignment bore 128 defined therein that extends from the component-engaging side 102 to the back side 104. The alignment bore 128 may be used to secure another surgical instrument to the impaction guide 100, for example, an alignment rod 144 as discussed below.

As described above, the impaction guide 100 includes a collar 108 that extends away from the cup 106. As shown in FIG. 3, the collar 108 has a truncated cone shape, and an aperture 130 is defined in back end of the collar 108. As described in greater detail below, the aperture 130 is sized to receive an impaction handle 142. The aperture 130 is defined by an inner wall 132 that extends from the back end of the collar 108 to a partition wall 134. As shown in FIGS. 2 and 3, a circular central passageway 118 is defined through the back wall 116 of the cup 102 and the collar 108. The passageway 118 connects the opening 112 of the cup 106 with the aperture 130 of the collar 108.

A slot 136 extends through the anterior side of the collar 108 and opens into the aperture 130. The lower end of the slot 136 is defined by a recessed wall segment 140, which is positioned below the partition wall 134 and extends posteriorly. As shown in FIG. 3, the wall segment 140 and a flange 138 of the partition wall 134 cooperate to define a pocket 141 below the partition wall 134. As described in more detail below, the central passageway 118, flange 138, and the pocket 141 cooperate to allow the impaction handle 142 to secure the impaction guide 100.

Figure 6:
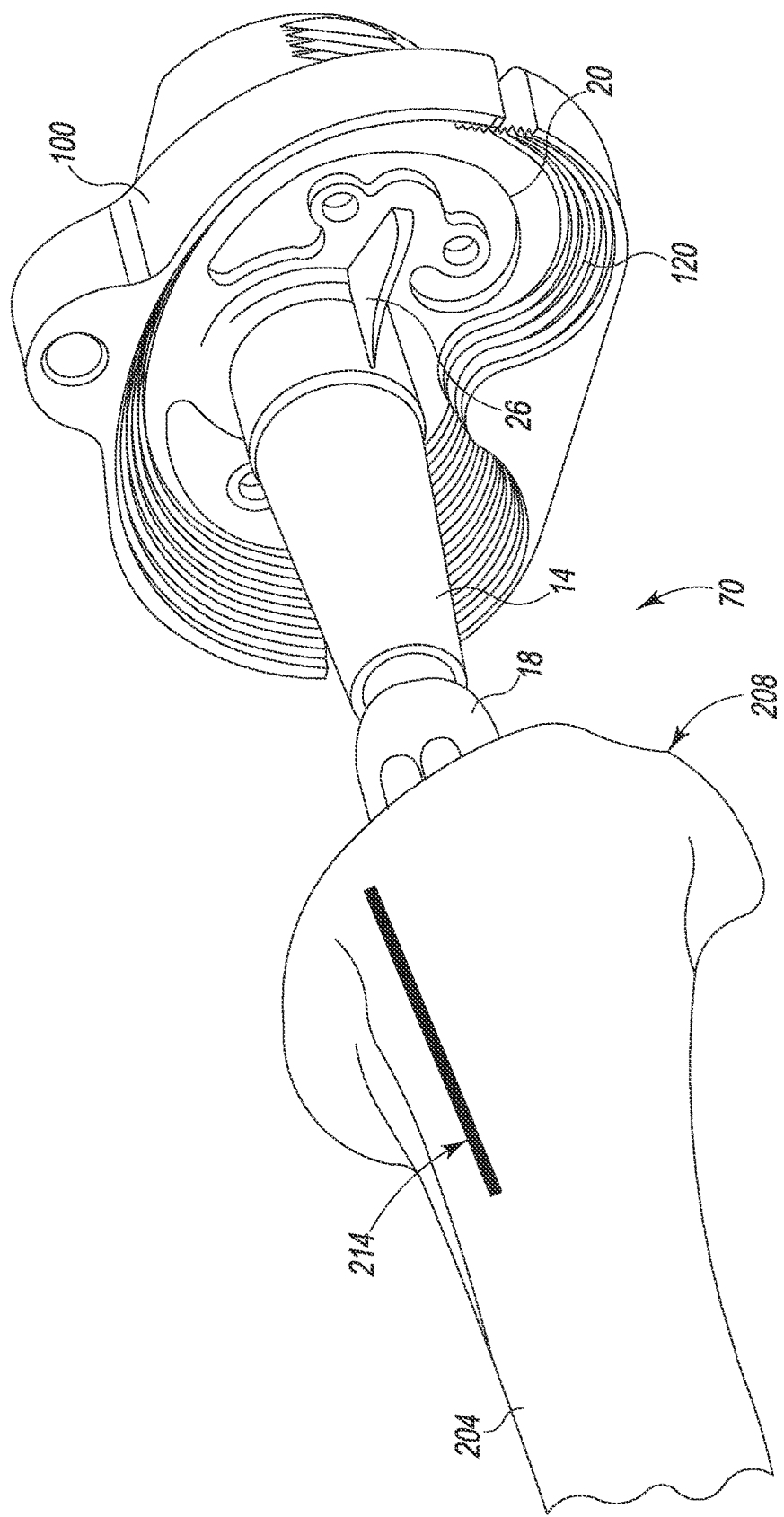
FIGS. 6-8 are views of a patient's tibia, the orthopaedic knee prosthesis of FIG. 1, the orthopaedic surgical instrument of FIGS. 2-5, and a group of orthopaedic instruments during the performance of an orthopaedic surgical procedure.

As described above, the impaction guide 100 may be attached to a tibial tray 14. For attachment, the tibial tray 14 is positioned with the platform 20 facing the component-engaging side 102 of the impaction guide 100. The tibial tray 14 is oriented so that the platform 20 aligns with one of the stepped surfaces 120 having the corresponding size. As the tibial tray 14 is brought into contact with the impaction guide 100, the platform 20 engages the corresponding stepped surface 120. The platform 20 is press-fit into the inner wall 114 against that stepped surface 120, thereby securing the tibial tray 14 to the impaction guide 100. When the tibial tray 14 and the impaction guide 100 are attached, the keels 26, 28 of the tibial tray 14 are aligned with the indicator (i.e., the slots 122, 124) of the impaction guide 100, as shown in FIG. 6. Thus, the slots 122, 124 may be used as visual alignment guides for the keels 26, 28.

Figure 7:
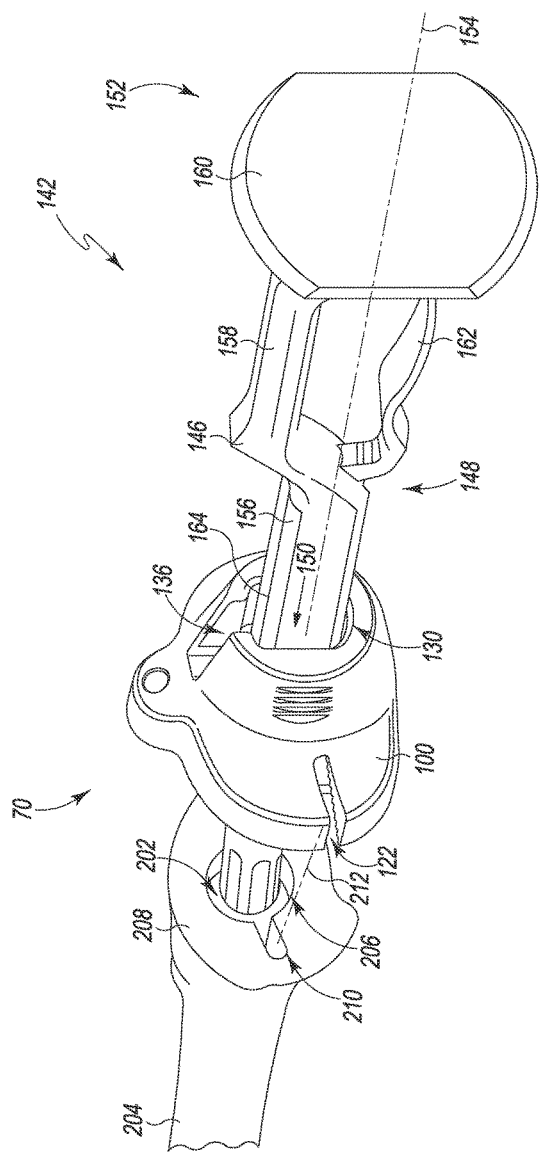

The impaction guide 100 additionally may be attached to a number of surgical instruments, including an impaction handle 142 and an alignment rod 144. As shown in FIG. 7, the impaction handle 142 includes an elongated tool body 146 and an attachment mechanism 148. The attachment mechanism 148 is configured to secure the impaction guide 100 to the impaction handle 142, as described in detail below. In the illustrative embodiment, the tool body 146 is formed from a metallic material, such as, for example, stainless steel or cobalt chromium.

The tool body 146 extends from an attachment end 150 to a strike end 152. A longitudinal axis 154 is defined between the attachment end 150 and the strike end 152. The tool body 146 includes a housing 156 positioned at the attachment end 150 and a grip 158 positioned adjacent to the housing 156 toward the strike end 152. The grip 158 is configured receive the hand of a surgeon or other user to allow the user to manipulate the impaction handle 142. Accordingly, the grip 158 may be coated in a rubberized or textured material to improve grip stability. In some embodiments, the grip 158 may be formed as a separate unit from the housing 156 and assembled with the housing 156 to form the tool body 146.

The impaction handle 142 further includes a strike plate 160 attached to the grip 158 at the strike end 152 of the tool body 146. The strike plate 160 is securely attached to the rest of the impaction handle 142, for example by mechanically threading onto the end of the grip 158. The strike plate 160 includes a durable surface suitable for use with a striking tool such as a mallet, sledge, or other impaction tool. The strike plate 160 is large enough to cover the grip 158 in order to shield the hand of the user. In use, the surgeon may impact the strike plate 160 to advance the tibial construct 70 into the intermedullary canal of the patient's tibia.

The impaction handle 142 includes a guide pin (not shown) extending from the attachment end 150 that is configured to be received by the central passageway 118 of the impaction guide 100. The attachment mechanism 148 of the impaction handle 142 includes the guide pin, a user-operated lever 162 extending outwardly from the housing 156 toward the strike end 152, and a catch 164 extending outwardly from the housing 156 toward the attachment end 150. The attachment mechanism 148 of the impaction handle 142 further includes an internal biasing element such as a spring (not shown) connecting the lever 162 and the catch 164. The lever 162 is moveable between an extended, unclamped position and the clamped position closer to the grip 158 shown in FIG. 7. When the lever 162 is moved by the user from the unclamped position to the clamped position, the catch 164 moves from a position apart from the guide pin to a position closer to the guide pin.

The impaction guide 100 may be attached to the impaction handle 142 by aligning the attachment end 150 of the impaction handle 142 with the aperture 130 of the collar 108. In the illustrative embodiment, the housing 156 is keyed to assist in aligning the impaction handle 142. The impaction handle 142 may then be advanced toward the guide 100 with the lever 162 in the unclamped position. As the attachment end 150 of the impaction handle 142 enters the aperture 130, the guide pin of the handle 142 is aligned with the central passageway 118 defined at the bottom of the aperture 130. The guide pin may be advanced into the central passageway 118 until the attachment end 150 of the tool body 146 engages the partition wall 134 of the impaction guide 100.

Concurrently, the catch 164 passes over the flange 138 of the guide 100 to a position adjacent to the recessed wall segment 140. The grip 158 and the lever 162 of the impaction handle 142 may be squeezed together to move the lever 162 to the clamped position, thereby causing the catch 164 to advance into the pocket 141 and engage the flange 138. When the catch 164 engages the flange 138, the impaction guide 100 is secured to the impaction handle 142. Further, when the lever 162 is in the clamped position, the internal biasing element of the impaction handle 142 provides clamping force to secure the impaction guide 100 to the impaction handle 142.

Figure 8:
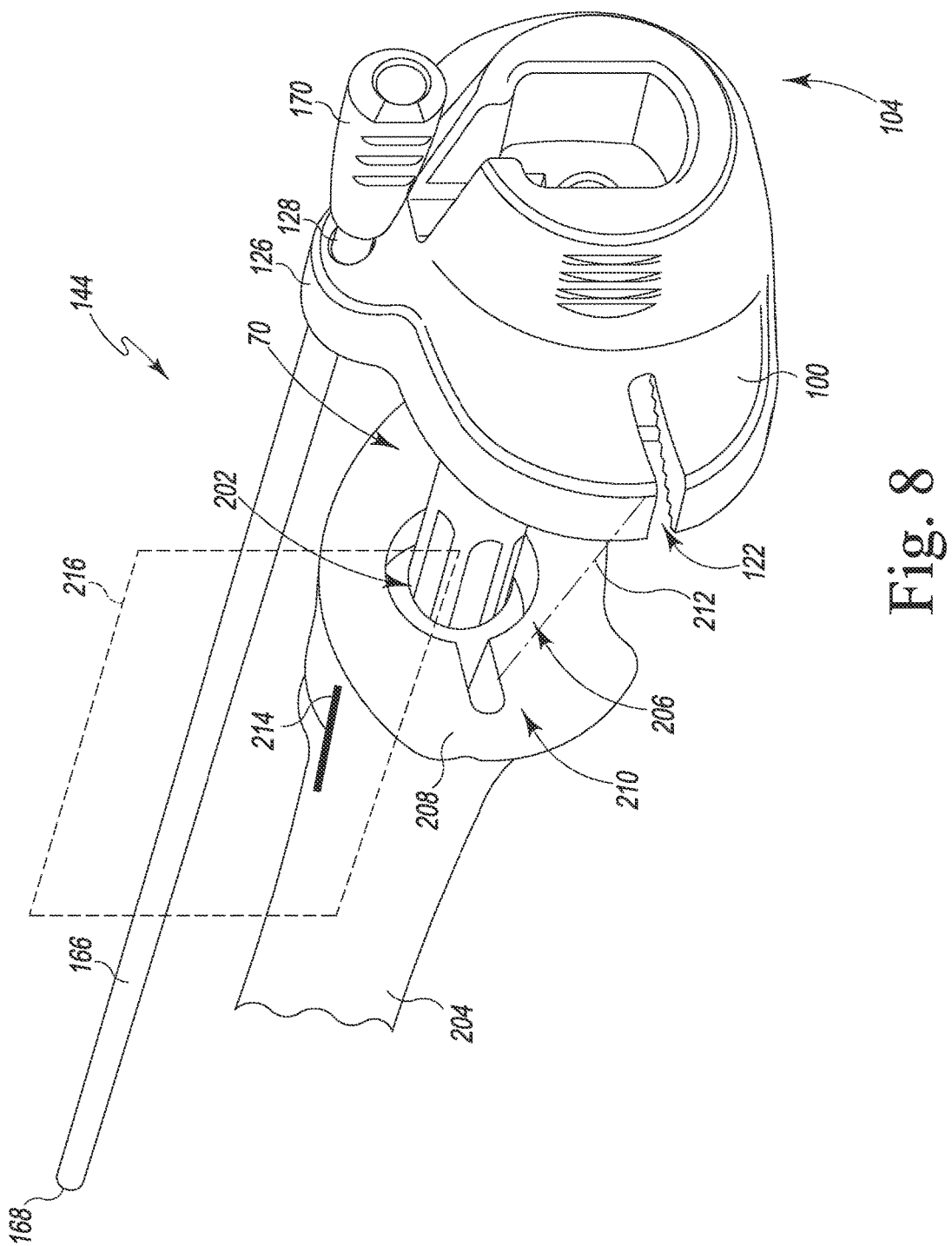

As described above, the impaction guide 100 may also be attached to an alignment rod 144. As shown in FIG. 8, the alignment rod 144 includes an elongated shaft 166 extending from a rounded end 168 to a grip 170. The grip 170 is wider than the shaft 166, and may include a textured surface configured to allow the user to manipulate the alignment rod 144.

The alignment rod 144 is attached to the impaction guide 100 by inserting the rounded end 168 of the alignment rod 144 into the alignment bore 128 of the impaction guide 100. The alignment rod 144 is advanced through the alignment bore 128 until the grip 170 engages the boss 126 of the impaction guide 100, as shown in FIG. 8. The boss 126 thus prevents the alignment rod 144 from continuing to advance through the alignment bore 128. Further, the shaft 166 and/or the grip 170 may include a tapered outer surface to lock the alignment rod 144 in position within the alignment bore 128.

The impaction guide 100 may be utilized during the performance of an orthopaedic surgical procedure similar to that shown in FIGS. 6-8. As shown in FIG. 6, the surgeon may insert an assembled tibial construct 70 into the impaction guide 100 and insert the tibial construct 70 into the intermedullary canal of the patient's tibia. As shown in FIG. 7, the surgeon may adjust the axial alignment of the tibial construct 70 using the impaction guide 100 and the attached impaction handle 142. As shown in FIG. 8, the surgeon may also adjust the axial alignment of the tibial construct 70 using the impaction guide 100 and an attached alignment rod 144.

The surgeon initially prepares the intermedullary canal 202 of the patient's tibia 204 to receive the tibial construct 70. To do so, the surgeon may insert an initial surgical reamer into the intermedullary canal 202. The surgeon may use the reamer to drill and/or ream the intermedullary canal 202 to the depth and/or diameter required to receive the stem component 18. Multiple drills or reamers may be used to increase the size of the opening 206 of the intermedullary canal 202 formed on the proximal surface 208 of the patient's tibia 204. The surgeon may further insert a surgical broach into the intermedullary canal 202 to cut and/or shape the intermedullary canal 202 to receive the sleeve component 46.

The surgeon further prepares the intermedullary canal 202 by cutting one or more slots 210 in the proximal surface 208, extending from the intermedullary canal 202 into the surrounding bone. The slots 210 are sized to receive the keels 26, 28 of the tibial tray 14, thereby stabilizing the tibial tray 14 when implanted. The surgeon may form the slots 210 by driving a keel punch tool into the proximal surface 208 of the tibia 204. When the surgical preparation is complete, the intermedullary canal 202 is configured as shown in FIGS. 7 and 8 and is ready to receive the tibial construct 70. A suitable method of preparing the intermedullary canal 202 of the tibia 204 is shown and described in U.S. patent application Ser. No. 13/485,444 entitled "METHOD OF SURGICALLY PREPARING A PATIENT'S TIBIA," which is incorporated herein by reference.

After preparing the intermedullary canal 202, the surgeon attaches the impaction guide 100 to the impaction handle 142. As described above, the surgeon may advance the attachment end 150 of the impaction handle 142 into the aperture 130 of the impaction guide 100. The surgeon advances the impaction handle 142 down the aperture 130 until a guide pin is received in the central passageway 118 of the impaction guide 100 and the attachment end 150 is seated against the partition wall 134. Once in position, the surgeon moves the lever 162 from the unclamped position to the clamped position to engage the catch 164 of the impaction handle 142 with the flange 138 of the impaction guide 100, thereby securing the impaction guide 100 to the impaction handle 142.

The surgeon may also assemble the tibial construct 70 to be attached to the impaction guide 100. The surgeon may select a tibial tray 14 and a stem component 18 of appropriate size for a particular patient, which may be determined using a trial reduction procedure. That is, the surgeon may try various combinations of prosthetic components to determine which implant size and configuration will have the best stability in flexion and extension while permitting the desired kinematics. Similarly, the surgeon may select an appropriate sleeve component 46 or a stem adaptor 48. This selection of components may be performed pre-operatively or intraoperatively, and may depend on the condition of the patient's tibia 204. After selection, the surgeon may assemble the tibial construct 70 from the selected tibial tray 14, stem component 18, and optional sleeve component 46 and/or stem adaptor 48.

As shown in FIG. 6, the surgeon may fit the platform 20 of the selected tibial tray 14 into one of the stepped surfaces 120 of the impaction guide 100. As described above, the surgeon press-fits the platform 20 into the stepped surface 120 having matching size.

After fitting the platform 20 to the impaction guide 100, the surgeon may insert the stem component 18 into the surgically prepared intermedullary canal 202 of the tibia 204, as shown in FIG. 7. As the stem component 18 is inserted into the intermedullary canal 202, the surgeon may rotate the impaction handle 142 axially about its longitudinal axis 154 to align the keels 26, 28 of the tibial tray 14 with the slots 210 of the intermedullary canal 202. The surgeon may rotate the impaction handle 142—and therefore also rotate the impaction guide 100 and the tibial construct 70—until the slots 210 of the intermedullary canal 202 are visible through the slots 122, 124 defined in the impaction guide 100, as indicated by sight line 212. Because the slots 122, 124 align with the keels 26, 28, when the slots 210 are visible through the slots 122, 124, the tibial construct 70 is properly aligned with the slots 210. It should be appreciated that in other embodiments the surgeon may draw or etch one or more lines on the proximal end of the tibia, which extend from (and are aligned with) the slot to the edge of the tibia to provide an indicator on the bone of the slot locations.

Additionally or alternatively to using the slots 122, 124 to align the impaction guide 100, the surgeon may use an attached alignment rod 144 to align the impaction guide 100. If so, prior to inserting the stem component 18 into the intermedullary canal 202, the surgeon may make a marking 214 on the anterior-most aspect of the tibia 204 (see FIG. 6). The surgeon may make the marking 214 using a marking tool such as a surgical marking pen, an electrosurgical generator tool, or any other surgical tool capable of making a mark on the tibia 204. As shown in FIG. 8, the surgeon may attach the alignment rod 144 to the impaction guide 100 by sliding the shaft 166 of the alignment rod 144 through the alignment bore 128 from the back side 104 of the impaction guide 100.

As shown in FIG. 8, as the stem component 18 is inserted into the intermedullary canal 202, the surgeon may rotate the impaction handle 142 axially about its longitudinal axis 154 to align the shaft 166 of the alignment rod 144 with the marking 214 on the tibia 204. The surgeon may rotate the impaction handle 142—and therefore also rotate the impaction guide 100 and the tibial construct 70—until the shaft 166, the marking 214, and the center of the intermedullary canal 202 lie in a common imaginary plane 216. Aligning the alignment rod 144 with the marking 214 also aligns the keels 26, 28 with the slots 210 of the intermedullary canal 202, because the keels 26, 28 and the slots 210 share the same relative alignment to the alignment rod 144 and the marking 214, respectively.

After aligning the tibial construct 70 using the slots 122, 124 and/or the alignment rod 144, the surgeon may then drive the tibial construct 70 into the tibia 204 along the intermedullary canal 202 by striking the strike plate 160 of the impaction handle 142 with mallet, sledge, or other impaction tool. As the tibial construct 70 is driven into the bone, the flutes 66 of the stem component 18 cut into the patient's tibia 204 to stabilize the tibial construct 70 in the intermedullary canal 202. Thus, the surgeon may use the impaction guide 100 to align the tibial construct 70 as it is inserted into the intermedullary canal 202 and as it is initially driven into the tibia 204, both when the keels 26, 28 of the tibial tray 14 are some distance from the proximal surface 208 of the tibia 204. Alternatively, the surgeon may rotate the impaction handle 142 axially to align the tibial construct 70 while the stem component 18 is partially inserted in the intermedullary canal 202, as long as the stem component 18 has not been advanced too far into the intermedullary canal 202.

After the tibial construct 70 has been driven into the tibia 204, the surgeon may remove the impaction guide 100 from the platform 20 and continue implantation of the knee prosthesis 10.

It should be appreciated that in other embodiments the impaction guide may be utilized without the impaction handle. In such embodiments, the impaction guide attached to the tibial construct 70, and the tibial construct 70 aligned with the patient's tibia by hand.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument having a component-engaging side and a back side includes:
   a cup positioned on the component-engaging side, the cup including: (i) an outer surface having an opening positioned on the component-engaging side and (ii) an inner wall extending from the opening of the outer surface to a back wall, the inner wall having a plurality of stepped surfaces facing the component-engaging side,
   a slot defined in the cup that extends from the component-engaging side to the back side, through the outer surface and the inner wall, the slot being positioned on a medial side of the instrument, and
   a collar coupled to the outer surface of the cup toward the back side, the collar including (i) an opening toward the back side sized to receive an impaction handle and (ii) a flange positioned in the opening that is configured to be secured to the impaction handle,
   wherein each of the plurality of stepped surfaces is sized to receive a platform of a tibial tray.

2. The orthopaedic surgical instrument of claim 1, wherein:
   each of the plurality of stepped surfaces has a perimeter, and
   the perimeters of the plurality of stepped surfaces decrease as the inner wall extends from the opening to the back wall.

3. The orthopaedic surgical instrument of claim 2, wherein the back wall is sized to receive a platform of a tibial tray.

4. The orthopaedic surgical instrument of claim 2, wherein each of the plurality of stepped surfaces has a kidney-shaped perimeter configured to receive the platform of the tibial tray.

5. The orthopaedic surgical instrument of claim 1, wherein the slot is configured to align with a keel of the tibial tray when the tray is received on one of the stepped surfaces.

6. The orthopaedic surgical instrument of claim 1, further including a second slot defined in the cup that extends from the component-engaging side to the back side, through the outer surface and the inner wall of the cup, wherein the second slot is positioned on a lateral side of the instrument.

7. The orthopaedic surgical instrument of claim 1, wherein the instrument further includes:
   a boss positioned on an anterior side of the outer surface of the cup, and
   an elongated alignment bore defined in the boss extending from the component-engaging side to the back side, wherein the alignment bore is sized to receive a shaft of an alignment rod.

8. The orthopaedic surgical instrument of claim 1 further including a central aperture defined through the back wall of the cup and through the opening of the collar, wherein the central aperture is sized to receive a guide pin of the impaction handle and the flange is positioned adjacent to the central aperture.

9. The orthopaedic surgical instrument of claim 8, wherein the collar further includes a recessed wall positioned adjacent to the flange to a allow a catch of the impaction handle to engage the flange.

10. An orthopaedic surgical instrument having a component-engaging side and a back side includes:
   a cup positioned on the component-engaging side, the cup including: (i) an outer surface having an opening positioned on the component-engaging side and (ii) an inner wall extending from the opening of the outer surface to a back wall, the inner wall having a plurality of stepped surfaces facing the component-engaging side,
   a slot defined in the cup that extends from the component-engaging side to the back side, through the outer surface and the inner wall, the slot being positioned on a lateral side of the instrument, and
   a collar coupled to the outer surface of the cup toward the back side, the collar including (i) an opening toward the back side sized to receive an impaction handle and (ii) a flange positioned in the opening that is configured to be secured to the impaction handle,
   wherein each of the plurality of stepped surfaces is sized to receive a platform of a tibial tray.

11. The orthopaedic surgical instrument of claim 10, wherein:
   each of the plurality of stepped surfaces has a perimeter, and
   the perimeters of the plurality of stepped surfaces decrease as the inner wall extends from the opening to the back wall.

12. The orthopaedic surgical instrument of claim 10, wherein the back wall is sized to receive a platform of a tibial tray.

13. The orthopaedic surgical instrument of claim 10, wherein each of the plurality of stepped surfaces has a kidney-shaped perimeter configured to receive the platform of the tibial tray.

14. The orthopaedic surgical instrument of claim 10, wherein the slot is configured to align with a keel of the tibial tray when the tray is received on one of the stepped surfaces.

15. The orthopaedic surgical instrument of claim 10, further including a second slot defined in the cup that extends from the component-engaging side to the back side, through the outer surface and the inner wall of the cup.

16. The orthopaedic surgical instrument of claim 10, wherein the instrument further includes:
   a boss positioned on an anterior side of the outer surface of the cup, and
   an elongated alignment bore defined in the boss extending from the component-engaging side to the back side,
   wherein the alignment bore is sized to receive a shaft of an alignment rod.

17. The orthopaedic surgical instrument of claim 10 further including a central aperture defined through the back wall of the cup and through the opening of the collar, wherein the central aperture is sized to receive a guide pin of the impaction handle and the flange is positioned adjacent to the central aperture.

18. The orthopaedic surgical instrument of claim 17, wherein the collar further includes a recessed wall positioned adjacent to the flange to a allow a catch of the impaction handle to engage the flange.

19. An orthopaedic surgical instrument having a component-engaging side and a back side includes:
   a cup positioned on the component-engaging side, the cup including: (i) an outer surface having an opening positioned on the component-engaging side and (ii) an inner wall extending from the opening of the outer surface to a back wall, the inner wall having a plurality of stepped surfaces facing the component-engaging side, wherein each of the plurality of stepped surfaces is sized to receive a platform of a tibial tray,
   a slot defined in the cup that extends from the component-engaging side to the back side, through the outer surface and the inner wall,
   a collar coupled to the outer surface of the cup toward the back side, the collar including (i) an opening toward the back side sized to receive an impaction handle and (ii) a flange positioned in the opening that is configured to be secured to the impaction handle,
   a boss positioned on an anterior side of the outer surface of the cup, and
   an elongated alignment bore defined in the boss extending from the component-engaging side to the back side,
   wherein the alignment bore is sized to receive a shaft of an alignment rod.

20. The orthopaedic surgical instrument of claim 19, wherein the slot is positioned on at least one of a lateral side or a medial side of the instrument.

* * * * *